United States Patent [19]

Mayes

[11] Patent Number: 5,397,026
[45] Date of Patent: Mar. 14, 1995

[54] METHOD FOR DISCHARGING CONTENTS OF A SEALED CONTAINER

[75] Inventor: Ronald A. Mayes, Beaumont, Tex.

[73] Assignee: Helena Laboratories Corporation, Tex.

[21] Appl. No.: 6,975

[22] Filed: Jan. 21, 1993

[51] Int. Cl.$^6$ .............................................. B67B 7/00
[52] U.S. Cl. ................................... 222/1; 222/82; 222/89; 222/207; 222/209; 222/420; 604/411
[58] Field of Search ............... 222/420, 207, 209, 211, 222/400.8, 401, 82-83, 85, 89; 604/411, 212, 217

[56] References Cited

U.S. PATENT DOCUMENTS

| | | | |
|---|---|---|---|
| 718,163 | 1/1903 | Sherrard | 222/82 |
| 2,431,192 | 11/1947 | Munson | 222/420 X |
| 2,730,270 | 1/1956 | Heinemann | 222/207 X |
| 3,369,708 | 2/1968 | Hein | 222/89 X |
| 4,779,767 | 10/1988 | Griffiths | 222/207 X |
| 5,163,583 | 11/1992 | Whitworth | 222/1 |

Primary Examiner—Andres Kashnikow
Assistant Examiner—Anthoula Pomrening
Attorney, Agent, or Firm—Spencer, Frank & Schneider

[57] ABSTRACT

An improved method and apparatus for discharging the contents of a test tube which has a resilient self-sealing, reusable stopper at one end. The apparatus includes a flexible member that has a constricted end and a second end. The constricted end defines an outlet area that has an opening. A support having an aperture is disposed proximate to the flexible member. The interior of the flexible member defines a cavity. The apparatus further includes a single fluid transfer tube having a longitudinal bore. The fluid transfer tube has a sharpened end for insertion into and through the seal of the test tube and an outlet end that extends into the aperture. The longitudinal bore establishes a fluid flow path from the sharpened end to the outlet end. When the fluid transfer tube is inserted into the seal of the test tube, the interior of the sealed test tube and the outlet area opening are in fluid communication.

3 Claims, 2 Drawing Sheets

METHOD FOR DISCHARGING CONTENTS OF A SEALED CONTAINER

BACKGROUND OF THE INVENTION

The present invention relates generally to a method and apparatus for discharging the contents of a sealed container and has particular utility in discharging the contents of a test tube, serum collection tube or the like. Tubes utilized for this purpose usually include a silica gel barrier. An anticoagulant is placed in the test tube, then a blood specimen is withdrawn from a patient and placed into the test tube, and finally the test tube is sealed with a resilient closure or stopper which is typically formed of rubber. The test tube and its contents are thereafter subject to temperature variations as well as centrifuging operations. During centrifuging, serum separates from whole blood with the serum positioned above the whole blood within the test tube. The silica gel barrier typically moves between the serum and the whole blood. This, of course, is conventional.

Three different approaches are known for handling the blood within the test tube subsequent to the centrifuging operation. One approach, illustrated and described in U.S. Pat. No. 5,139,174, to Golias, issued Aug. 18, 1992, relates to the removal of the stopper from the test tube and the placing of a dispenser on the open top of the test tube. The dispenser is then squeezed or otherwise manipulated to expel one or more drops of blood onto a specimen plate.

When using this approach, namely, the provision of a dispenser on the open test tube, it is, of course, necessary to invert the test tube prior to discharging blood from the test tube.

There were, of course, potential problems associated with the removal of the stopper from the test tube such as the potential for contamination of the blood and exposure of the laboratory technician to any disease carried by the blood. Upon removal of the stopper, a phenomenon known as aerosoling causes a spray of minute particles from within the test tube to be expelled into the air. There is substantial present concern by the laboratory technician because of potential exposure to the HIV virus, hepatitis and other diseases which may be carried by the blood.

One solution to this problem is presented in application Ser. No. 07/746,413, to Sarrine, filed Aug. 16, 1991, which describes an apparatus for dispensing fluid from a container or test tube. In general terms, two transfer tubes such as cannulas or needles are held relative to a bulb or pump. Both cannulas puncture the rubber stopper or closure of the test tube. One of the transfer tubes acts as a vent between the interior of the bulb and the interior of the test tube. The other transfer tube establishes a fluid flow path from the interior of the test tube, through the bulb, and out onto a specimen plate or the like. To dispense fluid contained within the test tube, the test tube is inverted, so that the fluid covers the ends of the two cannulas. Upon compressing the bulb, air within the bulb is forced through the vent transfer tube and into the test tube. The resulting positive pressure within the test tube forces the fluid through the other transfer tube as previously described.

Another solution to the problem of aerosoling is described in U.S. Pat. No. 5,114,033, issued to Golias on May 19, 1992, wherein a method and apparatus for discharging the contents of a sealed container are described and illustrated. In general terms, a holder containing one or more cannulas or needles punctures the rubber stopper or closure of the test tube. One of the cannulas is connected to a compressible bulb or pump, and a delivery tube is inserted through the second cannula into the interior of the test tube. Then, upon compressing the bulb, air is introduced into the test tube and the contents of the test tube are pressurized and discharged through the delivery tube onto a specimen plate. This approach avoids the need for inverting the test tube since the delivery tube could be inserted to the desired depth depending upon whether serum or whole blood was to be dispensed. However, this approach did require the use of a separate delivery tube, which could increase the complexity and the cost of the apparatus.

Each of the foregoing patents and application are incorporated by reference.

SUMMARY OF THE INVENTION

It is an object of the present invention to provide an improved method and apparatus for discharging the contents of a test tube which has a resilient self-sealing, reusable, repuncturable, stopper at one end, using a single transfer tube and which avoids the problems of aerosoling and contamination while still providing the benefits of good tactile control of the rate and amount of discharge.

It is a further object of the invention to provide an apparatus that can be inexpensively manufactured, is easy to use, and is free of independently moving parts.

The above and other objects are accomplished according to the invention by the provision of an apparatus including a flexible member that has a constricted end and a second end. The constricted end defines an outlet area that has an opening. A support having an aperture is disposed proximate to the second end. A cavity is defined within the interior of the flexible member. The apparatus further includes a single fluid transfer tube having a longitudinal bore. The fluid transfer tube has a sharpened end for insertion into and through the seal of the test tube and has an outlet end in communication with the cavity. When the fluid transfer tube is inserted into the seal of the test tube, the interior of the sealed test tube and the outlet area of the flexible member are in fluid communication through the single fluid transfer tube.

The method of the present invention includes attaching the apparatus to a test tube such that the transfer tube punctures the test tube seal, closing the open outlet of the flexible member, inverting the test tube, squeezing or compressing the flexible member, opening the outlet of the flexible member, and thereafter repeatedly flexing and compressing the flexible member to provide a continuous flow, in the nature of sequential pulses. Alternatively, the flexible member may be compressed slightly to discharge individual droplets of fluid from the test tube.

BRIEF DESCRIPTION OF THE DRAWINGS

The foregoing objects and advantages of the present invention, together with other advantages which may be obtained by its use, will become more apparent reading the following detailed description of the invention taken in conjunction with the drawings.

In the drawings, wherein like reference numerals identify corresponding components.

DETAILED DESCRIPTION OF THE INVENTION

Figure 1:
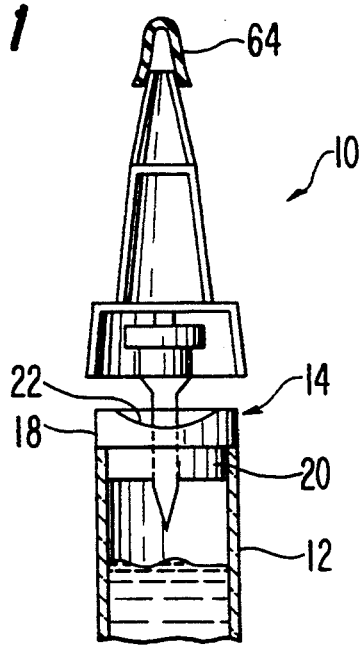
FIG. 1 is an illustration, partly in section, of a portion of a test tube, a test tube stopper and the apparatus of the present invention.
Figure 2:
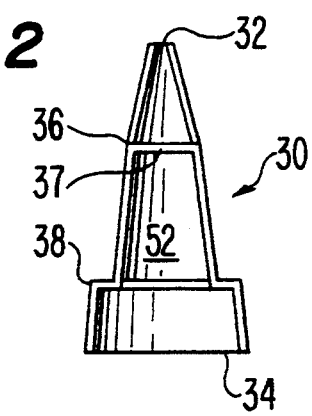
FIG. 2 is an illustration of one form of an elongated flexible member according to the present invention.
Figure 3:
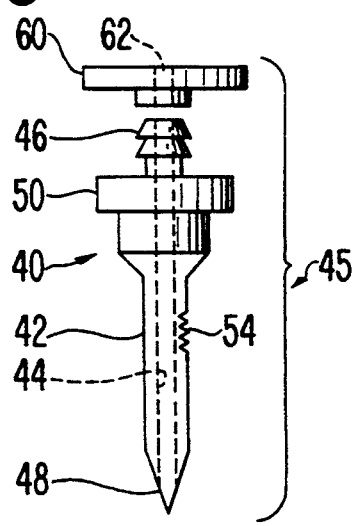
FIG. 3 is an illustration of a portion of the puncturing mechanism of the present invention.

With reference to the drawings, and more particularly FIG. 1, a dispenser assembly 10 is illustrated attached to a test tube 12, the top of the test tube being closed by a stopper 14. Test tube 12 may be a standard test tube, serum separator tube, collection tube or the like, formed of glass, and having a generally circular cross-section (in plan view) with a rounded end or bottom 16. The stopper 14 is a resilient, self-sealing, reusable, repuncturable member which is also of circular cross-section (in plan view) having an enlarged head 18 and a stem section 20. The stopper is configured to frictionally, resiliently, sealingly engage the interior wall of the test tube 12 as well as to engage the test tube rim as is conventional. Also, as is conventional, the top central portion of the stopper head may include a slight recess 22.

The dispenser assembly 10 includes a resilient elongated, flexible, member 30 which may be preferably formed of low density polyethylene, having first and second ends 32, 34, respectively. The elongated member 30 is thin walled and has a generally circular configuration (in plan view) and a generally increasing diameter from the first end to the second end in the embodiment of FIGS. 1-4. In that illustrated embodiment, the elongated member 30 increases in diameter from the open first end 32 to a first fluid constriction region 36 at which point the degree of increase of the diameter is reduced slightly, and the dispensing member continues to a second fluid constricting portion 38 where the dispensing member includes a radially outward shoulder. A paper filter, or the like, 37 may be included interiorly of the dispensing member at the first fluid constricting portion 36.

Means are provided as part of the dispenser assembly 10 for puncturing the stopper 14 which is associated with the test tube 12. In the illustrated embodiment of FIGS. 1-4, a puncturing means 40 is illustrated as including a barb 42 of impact polystyrene of generally elongated configuration having a longitudinal bore 44 therethrough. Barb 42 and bore 44 partially define a fluid transfer path 45 or fluid transfer means. The bore 44 extends from the upper portion 46 of the puncturing means and continues through to the bottom or tip of 48 of the barb. The barb tip 48 may be sharpened or curved to facilitate puncturing the stopper 14. Longitudinally inwardly of the barb top 46 is an enlarged head 50.

The upper portion of the barb 46 is provided with a plurality of teeth, of generally circular cross-section, for securing the puncturing means to the elongated flexible member 30 as will be hereinafter described. The side of the barb also includes a plurality of barb teeth 54 to prevent inadvertent removal of the barb from the stopper.

A disc 60 of generally circular configuration, which may be formed of nylon or preferably a low density polyethylene, and having an aperture or bore 62 therethrough, is secured to the top of the puncturing means 40 such as by sonic welding, bonding or the like. The diameter of the disc 60 is configured to fit snugly within the second fluid constriction 38 of the elongated hollow flexible member 30 and is secured thereto by sonic welding, bonding or the like. The disc 60 prevents fluid from entering the elongated member 30 except through the disc bore 62. A cap 64 is provided for the first end 32 of the flexible member 30. Cap 64 is designed to frictionally close the first end 32 of the dispenser assembly.

The barb has tapered side walls to provide a self-centering function when the puncturing means is inserted into the top of the seal or stopper 14.

After blood has been collected in the collection tube or test tube 12, the stopper 14 is inserted to close the top of the tube, and the blood is subjected to a centrifuging operation, all as conventional. The dispenser assembly 10, including the elongated resilient member 30 having the puncturing means 40 attached thereto, is inserted into the test tube stopper 14 such that the barb 42 and more particularly the barb tip 48 punctures the stopper. The barb is of a sufficient length to extend through the stopper such that the bottom of the bore 44 in the puncturing means 40 extends below the bottom of the stopper stem 20. A fluid flow path 45 is thus provided through the bore 44 of the barb 42 and through the bore 62 of the disc 60 into the interior of the flexible elongated hollow member.

In describing the operation of the present invention, it should be appreciated and understood that when the dispenser assembly is inserted on the test tube and punctures the test tube stopper, air will be present within the dispenser assembly.

Figure 4:
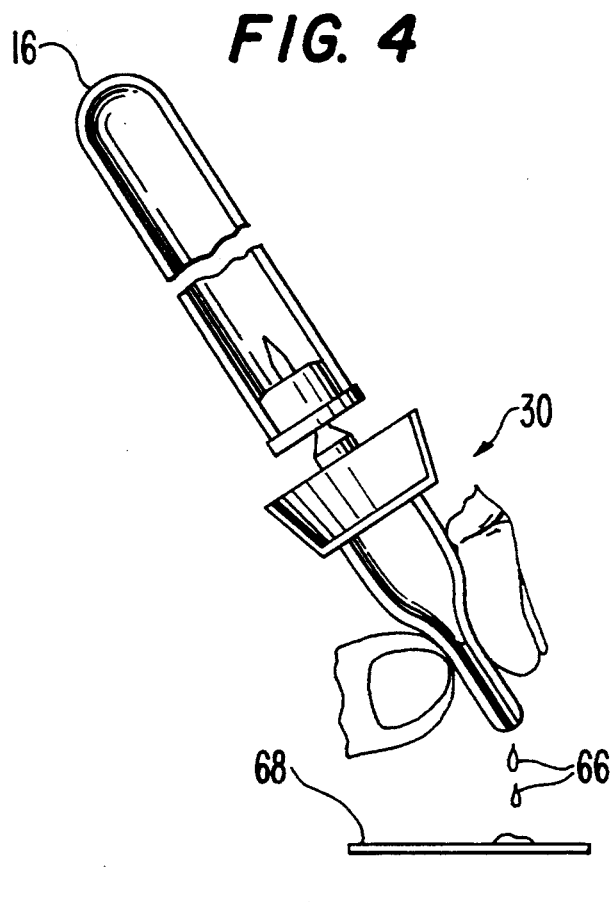
FIG. 4 is an illustration of the utilization of the present invention.

In one method of dispensing, with the cap 64 in place, or the outlet 32 manually covered, the combined test tube and dispenser assembly is inverted as illustrated in Figure 4, such that the liquid contained within test tube 16 rises to a level to cover barb tip 48. A cavity 52 is defined interiorly of the flexible member. The resilient elongated member 30 is compressed or squeezed. Air contained within cavity 52 is forced into test tube 16, creating a positive pressure therein. The compressing of resilient elongated member 30 ceases and the resilient member is released to return to its original non-compressed configuration. The positive pressure within test tube 12 forces the fluid within test tube 12 through bore 44, and into cavity 52. Cap 64 is removed, and the fluid within cavity 52 is dispensed onto a specimen plate 68 or the like by again compressing or squeezing or flexing elongated member 30 slowly. This provides dispensing of fluid in a drop-by-drop method.

An alternate method of dispensing fluid will now be explained. To understand the alternate method, additional details of the apparatus must first be understood. In this method of use of the apparatus (with reference to FIGS. 14) the diameter (or more generally the cross-sectional area) of bore 44 is larger than the diameter (or more generally the cross-sectional area) of the opening at first end 32. With respect to one technique according to the principles of the present invention, with cap 64 removed, the combined test tube and dispenser assembly is inverted generally to the orientation illustrated in FIG. 4. By squeezing or flexing the resilient elongated member 30 rapidly, one or more drops 66 of the fluid will flow from the interior of the test tube through the bore 44 in the puncturing means, and into the hollow elongated flexible member 30 for subsequent dispensing onto a specimen plate 68 or the like. Since the cross-sectional area of bore 44 is larger than the cross-sectional area of outlet 32, when elongated member 30 is rapidly repeatedly compressed, and released, during each compression step some of the air within cavity 52 will be forced through bore 44 and into test tube 12. This will create a positive pressure within the interior of test tube 12, forcing the fluid through bore 44 and into cavity 52. In effect, bore 44 is acting as a liquid transfer tube and a vent, simultaneously. Thus a pumping or pulsing action occurs with fluid discharged (and air entering the test tube simultaneously) upon each compression of the flexible member.

In yet an another alternate method utilizing the apparatus of FIGS. 1-4, again with the aforementioned relationship between the cross-sectional areas being maintained as described, cap 64 may be kept in place after inversion of the combined test tube and dispenser assembly. When resilient elongated member 30 is compressed, some of the air contained within cavity 52 will be forced through the bore 44 into test tube 12, creating a positive pressure therein. The compressing of resilient elongated member 30 is then terminated. The positive pressure within test tube 12 forces some of the fluid within test tube 12 through bore 44, out of aperture 62, and into cavity 52. Cap 64 is then removed, and resilient elongated member 30 is again compressed. Because fluid in the cavity covers the opening 32, a back pressure is created within cavity 52. As a result, when elongated member 30 is again compressed, some of the air within cavity 52 will be forced through bore 44 and into test tube 12. This will create a positive pressure within the interior of test tube 12, resulting in the simultaneous forcing of some of the fluid through bore 44 and into cavity 52. Concurrent with this action, some of the fluid already within cavity 52 will be dispensed through the opening at first end 32. In this manner, the fluid level within cavity 52 will remain below aperture 62 and thus aperture 62 will not be closed by fluid. Resilient elongated member 30 may be repeatedly compressed (and alternately released) until the entire contents of test tube 16 are dispensed.

Figure 5:
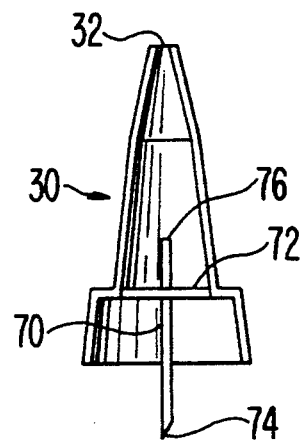
FIG. 5 is an illustration of a second form of the present invention.

Referring next to FIG. 5, another embodiment of the present invention is disclosed. In this embodiment, the fluid transfer means is illustrated as a single, hollow, elongated tube 70 mounted within a support disc or support means 72. In this embodiment, the fluid transfer means has first and second ends 74, 76 which extend outwardly from opposite sides of the support disc. Hence the support disc may be provided with an internal aperture to receive the transfer tube therethrough. The transfer tube 70 may be formed of plastic as previously described, or formed of metal, and may be sharpened at the first end 74 to facilitate puncturing the stopper 14 of the test tube 12. The operation of the apparatus of FIG. 5, including the various optional methods of use, is consistent with the embodiment of FIGS. 1-4.

Figure 6:
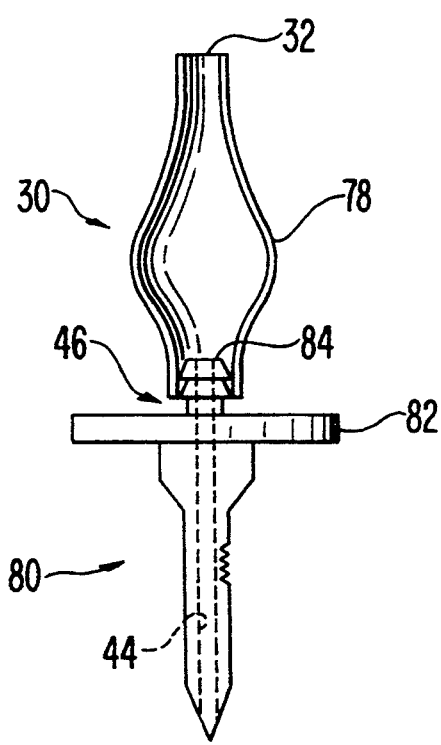
FIG. 6 is an illustration of a third and preferred form of the present invention.

FIG. 6 illustrates a preferred embodiment of the present invention including a bulbous flexible member 78 mounted on one end of a puncturing means 80. The puncturing means is an impact polystyrene member configured generally the same as the puncturing means 40 of FIGS. 1-4 except that instead of the support means or support disc 60 (of the embodiment of FIGS. 1-4), the embodiment of FIG. 6 includes a support means 82 formed intermediate the ends of the puncturing means. The puncturing means includes the bore 44 thus providing the fluid transfer tube or fluid transfer means. In this embodiment of FIG. 6, the bulbous, flexible member is mounted on the upper circular teeth 84 at first end 46 of the of the barb 80 (corresponding to the teeth in FIG. 3). Again, the various modes of operation of the embodiment of FIG. 6 correspond to the various modes of operation previously discussed in relation to the embodiment of FIGS. 1-4.

Many changes and modifications may be made without departing from the spirit and scope of the present invention. The invention, therefore, should be limited only by the following claims.

What is claimed is:

1. A method for dispensing fluid from a repuncturable, sealed test tube using a dispenser having first and second ends, a flexible member, a single fluid transfer tube, and an outlet, comprising:
   inserting said first end of the dispenser through the seal of a test tube which contains fluid to be dispensed;
   blocking said dispenser outlet to prevent the flow of fluid therethrough;
   inverting said dispenser and the attached test tube such that the fluid contained within the test tube reaches a level above said first end of said dispenser;
   compressing said flexible member such that air contained within said flexible member is forced through said fluid transfer tube into the test tube;
   unblocking said dispenser outlet; and
   compressing said flexible member wherein some of the air contained within said flexible member is forced through said single fluid transfer tube into the test tube, and some of the fluid contained within the test tube is simultaneously pumped in the opposite direction through said single fluid transfer tube and into said flexible member, and wherein some of the fluid contained within said flexible member is simultaneously transferred outwardly of said dispenser.

2. The method as defined in claim 1, wherein said blocking step includes providing a cap to block said dispenser outlet.

3. The method as defined in claim 1, further comprising the step of providing said dispenser with mean for resisting removal of said first end from the sealed test tube.

* * * * *